United States Patent [19]

May et al.

[11] Patent Number: 5,026,398

[45] Date of Patent: Jun. 25, 1991

[54] ABRASION RESISTANT PROSTHETIC DEVICE

[75] Inventors: Steven J. May, Minnetonka; David J. Andrews, West St. Paul; Craig L. VanKampen, Oakdale, all of Minn.

[73] Assignee: The Minnesota Mining and Manufacturing Company, Saint Paul, Minn.

[21] Appl. No.: 595,641

[22] Filed: Oct. 9, 1990

Related U.S. Application Data

[63] Continuation of Ser. No. 214,699, Jul. 1, 1988, abandoned.

[51] Int. Cl.$^5$ .............................................. A61F 2/08
[52] U.S. Cl. ...................................... 623/13; 606/151
[58] Field of Search .......................... 623/13; 606/151

[56] References Cited

U.S. PATENT DOCUMENTS

| | | | |
|---|---|---|---|
| 3,797,047 | 3/1974 | Pillet | 623/13 |
| 4,187,558 | 2/1980 | Dahlen et al. | |
| 4,209,859 | 7/1980 | Hoffman | |
| 4,246,660 | 1/1981 | Wevers | |
| 4,301,551 | 11/1981 | Dore et al. | |
| 4,345,339 | 8/1982 | Muller et al. | |
| 4,411,027 | 10/1983 | Alexander et al. | |
| 4,483,023 | 11/1984 | Hoffman, Jr. et al. | |
| 4,584,722 | 4/1986 | Levy et al. | 623/13 |
| 4,744,793 | 5/1988 | Parr et al. | 623/13 |
| 4,759,765 | 7/1988 | VanKampen | 623/13 |
| 4,773,910 | 9/1988 | Chen et al. | |

FOREIGN PATENT DOCUMENTS

| | | |
|---|---|---|
| 106501 | 4/1984 | European Pat. Off. |
| 122744 | 9/1984 | European Pat. Off. |
| 126520 | 11/1984 | European Pat. Off. |
| 0145492 | 6/1985 | European Pat. Off. |
| 192949 | 3/1986 | European Pat. Off. |
| 238263 | 9/1987 | European Pat. Off. |
| 2510394 | 2/1983 | France |
| 84/04669 | 12/1984 | World Int. Prop. O. |

OTHER PUBLICATIONS

"Experimental Mechanical and Histologic Evaluation of the Kennedy Ligament Augmentation Device", in Clinical Orthopaedics, by G. K. McPherson, et al., Jun., 1985.

Primary Examiner—Alan Cannon
Attorney, Agent, or Firm—Kinney & Lange

[57] ABSTRACT

An abrasion resistant prosthetic ligament or tendon includes a strap-like element formed of a stable biocompatible material which is attached at opposite ends to a patient. Attached to the strap-like element are one or more protective layers having sacrificial areas which are positioned in areas where abrasion between the prosthetic ligament and the patient's bones is anticipated. The sacrificial areas can be substantially abraided before any significant loss of strenth occurs, because the sacrificial areas are non-load-bearing, and protect the strap-like element from abrasion.

23 Claims, 3 Drawing Sheets

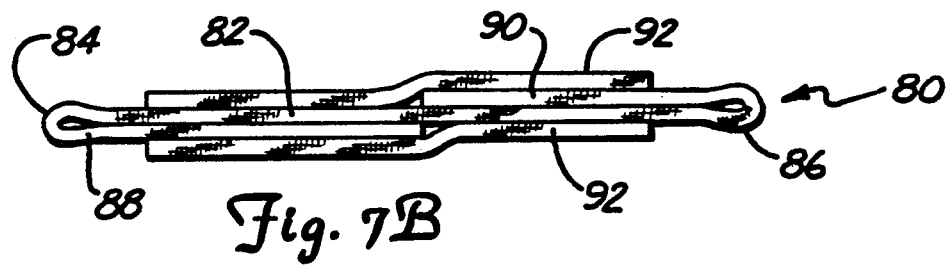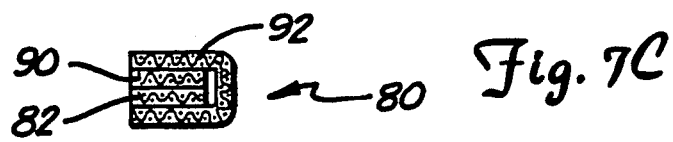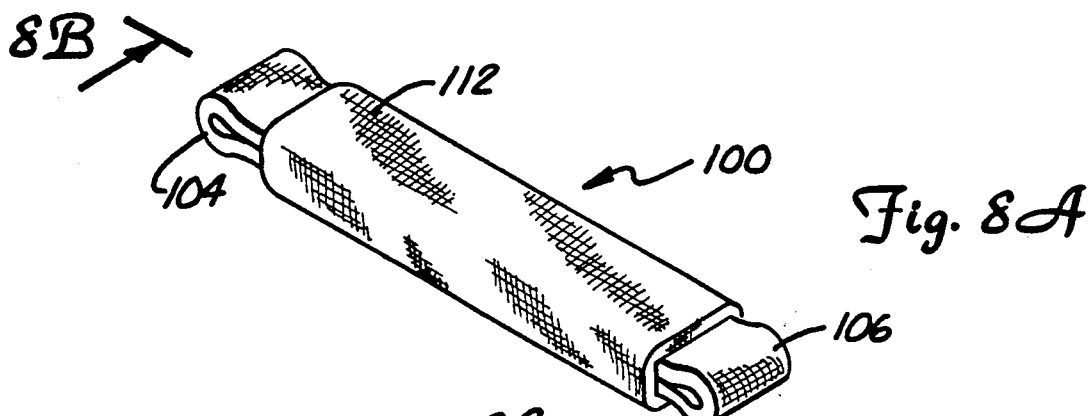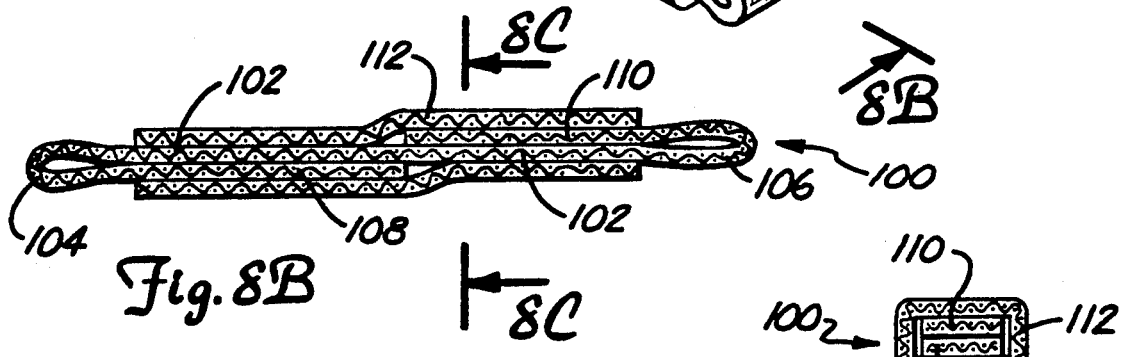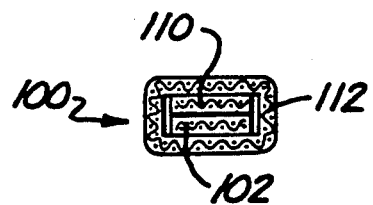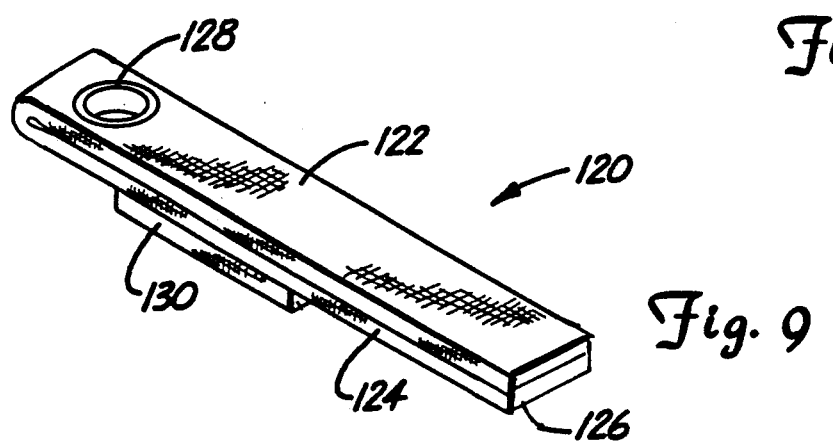

ABRASION RESISTANT PROSTHETIC DEVICE

This is a continuation of application Ser. No. 214,699 filed on July 1, 1988, abandoned as of the date of this application.

BACKGROUND OF THE INVENTION

1. Field of the Invention

The present invention relates to devices and methods for replacing damaged biological tissue such as ligaments and tendons.

2. Description of the Prior Art

Current methods for replacement of ligaments and tendons too badly damaged to be repaired include replacement with natural biological tissue (such as skin, facia or tendon) and replacement with artificial materials.

One example of ligament reconstruction is the replacement of the anterior cruciate ligament (ACL) of the knee. The ACL provides knee stability by extending intra-articularly across the knee joint from the anteromedial surface of the proximal tibia to the posterolateral surface of the distal femur. An ACL replacement prosthesis must be implanted in the appropriate anatomical position in order to restore knee stability. This may be achieved by drilling holes in the tibia and femur that exit intra-articularly at the normal anatomic attachment sites of the ACL. An alternative to the femoral drill hole is to place the ACL replacement prosthesis over the lateral femoral condyle, which is often referred to as the "over-the-top" position.

An important problem associated with knee ligament prostheses relates to the abrasion and eventual rupture of the device. The anatomical constraints which necessitate the use of a tibial drill hole and either a femoral drill hole or an over-the-top arrangement of the ligament prosthesis also necessitate that the prosthesis be in contact with bone. This bone contact presents an unavoidable source for abrasion of the device. Abrasion rupture is the principal failure mechanism of prosthetic ligaments.

SUMMARY OF THE INVENTION

The present invention is based upon our discovery that the problem of prosthetic ligament abrasion can be significantly diminished by a prosthetic ligament formed by a strap-like element having sacrificial abrasion layers attached at critical abrasion areas. The sacrificial layers can be abraided substantially with only minimal strength loss to the strap-like element (and therefore, with minimal effect to the load-bearing capabilities of the prosthetic device). This ability to withstand a substantial amount of abrasion without significant strength loss enables the prosthetic device of the present invention to maintain its original mechanical properties for extended time periods.

BRIEF DESCRIPTION OF THE DRAWINGS

FIG. 7A, 7B and 7C are perspective, side elevational and sectional views of a third embodiment of the prosthetic ligament of the present invention.

FIGS. 8A, 8B and 8C are perspective and sectional views of a fourth embodiment of the prosthetic ligament of the present invention.

FIG. 9 is a perspective view of a fifth embodiment of the prosthetic device of the present invention.

DETAILED DESCRIPTION OF THE PREFERRED EMBODIMENTS

The prosthetic device of the present invention is used as a replacement for a damaged ligament or tendon. Generally, the device will be surgically implanted and anchored to bone by bone screws, sutures or staples.

Figure 1:
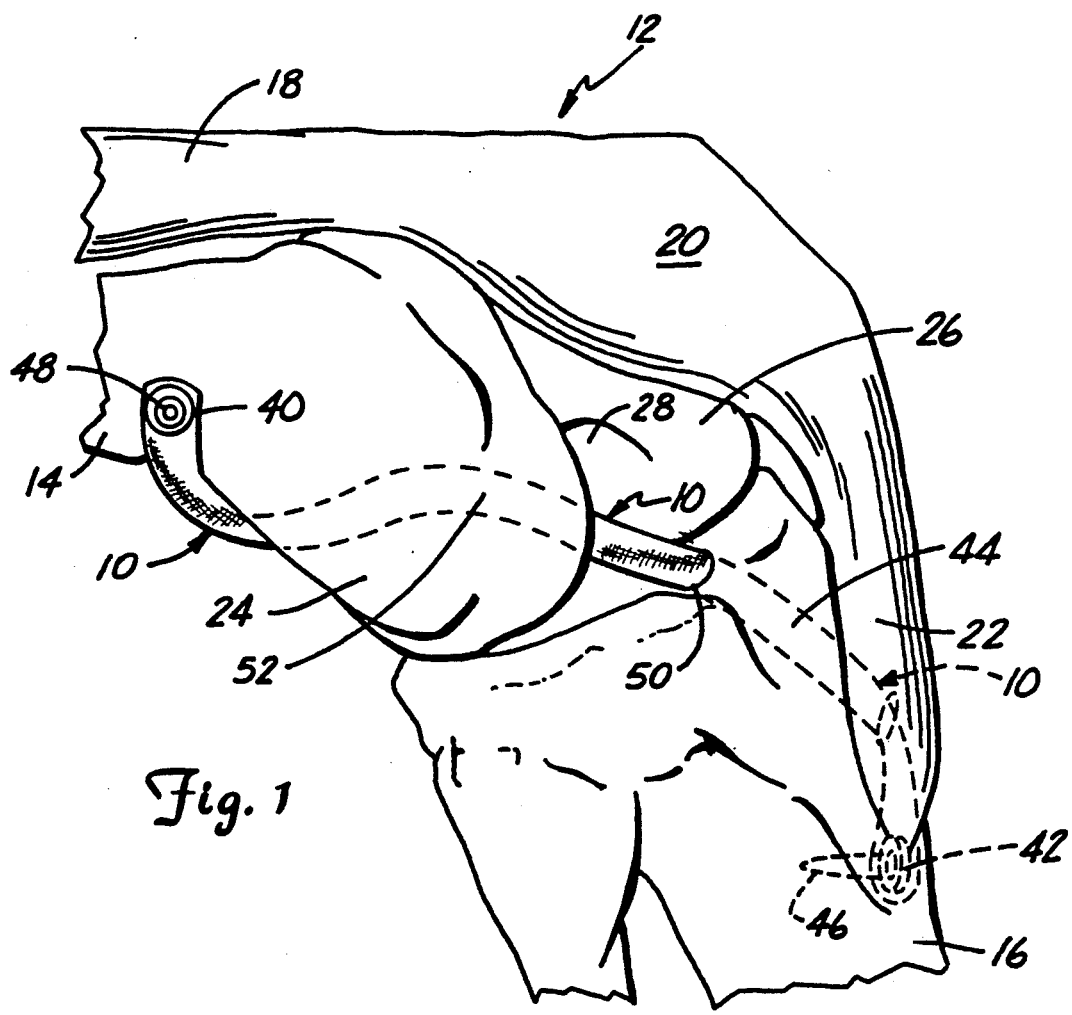
FIG. 1 is a lateral view of a knee joint showing the prosthetic ligament of the present invention in place.

One particularly advantageous use of the prosthetic device of the present invention is as a replacement for the anterior cruciate ligament of the knee. This use of the present invention is illustrated in FIG. 1, which shows prosthetic device 10 implanted as a replacement for the anterior cruciate ligament of knee 12. In FIG. 1, femur 14, tibia 16, quadriceps tendon 18, patella 20, and patellar tendon 22 are shown. Shown at the distal end of femur 14 are lateral femoral condyle 24, medial femoral condyle 26, and intercondylar notch 28.

Prosthetic device 10, which is shown in further detail in FIGS. 2-5, includes a flexible load-bearing strap-like element 30 which is folded over at each end to form end loops 32 and 34 and abrasion resistant sacrificial layers or areas 36 and 38. Attachment eyelets 40 and 42 extend through loops 32 and 34, respectively. When the term "sacrificial layers" is used herein, it should be understood to refer to the sacrificial areas of the layers, since the entire layer is not sacrificial, but a major portion of the layer which is not part of the end loop is sacrificial. The end loop portion of the sacrificial layer contributes substantially to the strength of the device and should not be sacrificed.

As shown in FIG. 1, eyelet 42 on the tibial end of device 10 remains outside of tibial drill hole tunnel 44 and is anchored to the anteromedial surface of the tibia 16 by bone screw 46. Device 10 extends upward from eyelet 42 through tibial bone tunnel 44 and then across lateral femoral condyle 24. Tension is applied to the femoral end of device 10 in order to restore normal knee joint laxity, and eyelet 40 of device 10 is then anchored to a lateral surface of femur 14 by bone screw 48.

As illustrated in FIG. 1, there are two primary abrasion sites, 50 and 52, where abrasion of prosthetic device 10 will occur due to friction between device 10 and bone. Abrasion site 50 is located at the posterior exit of tibial bone tunnel 44. Abrasion site 52 is a larger area in the over-the-top region where device 10 extends over lateral femoral condyle 24. Abrasion due to friction between bone and device 10 at abrasion sites 50 and 52 occurs on opposite sides of device 10.

Although not illustrated, use of a femoral drill hole rather than an over-the-top attachment of device 10 will also create an abrasion site where device 10 comes into frictional contact with femur 14 at the anterior exit of the femoral bone tunnel.

Prosthetic device 10 of the present invention is capable of withstanding substantial amounts of abrasion without significantly diminishing its load-bearing characteristics. This significantly extends the useful lifetime of prosthetic device 10 beyond the characteristics of prior art ligament and tendon prostheses.

In the preferred embodiment of device 10 shown in FIGS. 2-5, a unitary strap-like material is used to form load-bearing strap-like element 30, loops 32 and 34 and sacrificial layers 36 and 38. Strap-like element 30, which is the principal load-bearing element of device 10, is sandwiched between protective layers having sacrificial areas 36 and 38. Layers 36 and 38 shield load-bearing strap-like element 30 from excessive abrasion at abrasion sites 50 and 52. In particular, a portion of sacrificial layer 36 extending from approximately the midpoint between eyelets 40 and 42 to near eyelet 40 is positioned between strap-like element 30 and abrasion site 52. Similarly, a portion of sacrificial layer 38 from about the midpoint of device 10 to the end of sacrificial layer 38 near eyelet 42 protects strap-like element 30 from abrasion at abrasion site 50.

Sacrificial layers 36 and 38 are connected or bonded to strap-like element 30. In the preferred embodiment illustrated in FIGS. 2 and 3, three lines of parallel sewn stitches 54, 56, and 58 bond together strap-like element 30 and sacrificial layers 36 and 38.

Loops 32 and 34 provide additional strength to device 10 because eyelets 40 and 42 extend through two layers of material which are folded over to provide continuous fibers at the ends of the device.

In a preferred embodiment of the present invention, in which device 10 is made of a continuous strap-like material, the material is preferably formed from a braid similar to presently known ligament augmentation devices such as the Kennedy LAD ® braid ligament augmentation device described in U.S. Pat. application Ser. No. 840,374, which is assigned to the same assignee as the present application and which is hereby incorporated by reference.

The strap-like material is flexible and, in the preferred embodiment shown in FIG. 2-5, is generally flat in cross-section. Other cross-sectional geometries, however, also may be used with the present invention.

Device 10 must be biocompatible, i.e., it should be non-immunogenic, non-mutagenic, non-carcinogenic and elicit no chronic inflammatory response. To ensure biocompatibility, it is preferred to utilize suitable biomaterials which have a proven history in implanted devices.

In addition to biocompatibility, strap-like element 30 must have sufficient tensile strength to carry the working loads normally carried by a natural ligament or tendon being replaced and low flexural rigidity so as to be flexible enough to prevent interference with the normal movement of muscular or skeletal structures connected by prosthetic device 10. Strap-like element 30 must also maintain its mechanical properties over time, i.e., exhibit resistance to fatigue and creep and be stable in the moist environment of the body.

Materials which are suitable for fabricating the strap-like element 30 generally include synthetic polymeric materials which can be formed into high strength yarns. Such polymeric materials include, but are not limited to, polyolefins such as polypropylene, ultra high molecular weight polyethylene, and polybutylene; polyesters such as polyethylene terephthalate; polytetrafluoroethylene; and polyaramids.

To obtain high strength and flexibility, strap-like element 30 is preferably fabricated from yarns of the foregoing material. Braids, webbings or weaves of these yarns are preferred. Alternatively, some materials such as polybutylene may be fabricated into flat bands of high strength and flexibility.

One preferred braid used for strap-like element 30 consists of 26 bundles of high tenacity (7.5 g/denier) polypropylene filaments, with each bundle containing 180 filaments. These bundles are braided into a flat strap-like structure about 2 mm thick and 14 mm wide. After forming the strap-like material of desired length and configuration, the braid is cut and the ends are sealed to prevent unraveling.

A more open structure than that of the braid may offer certain advantages when used as strap-like element 30. For example, a more open structure permits viable tissue ingrowth throughout the length of device 10.

Figure 2:
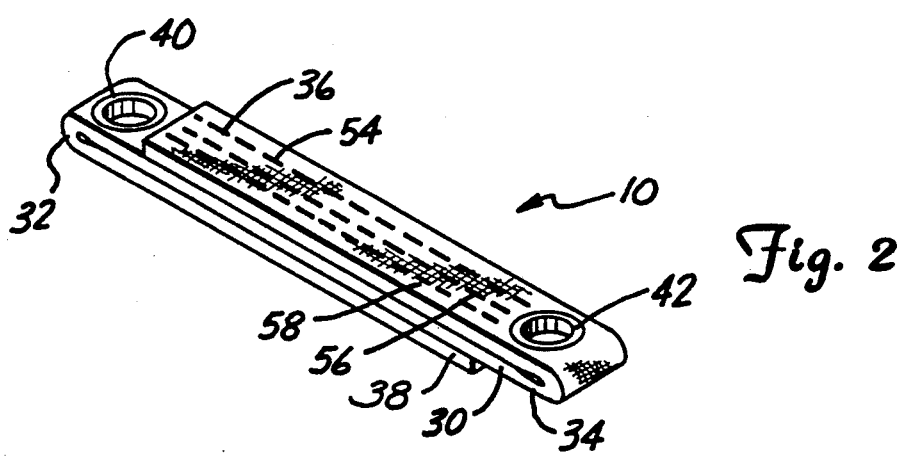
FIG. 2 is a perspective view of a preferred embodiment of the prosthetic ligament of the present invention.
Figure 3:
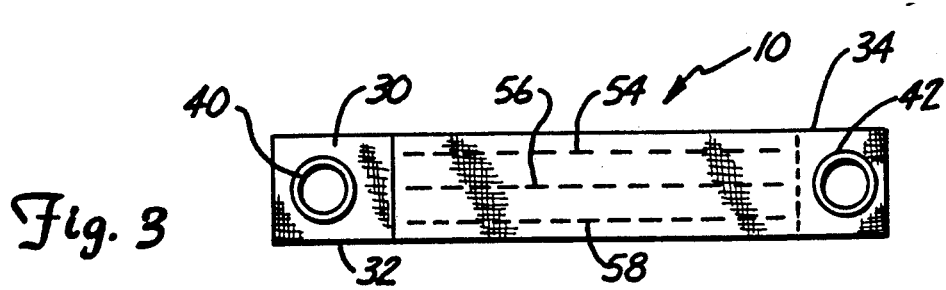
FIG. 3 is a top view of the prosthetic ligament of FIG. 2.
Figure 4:
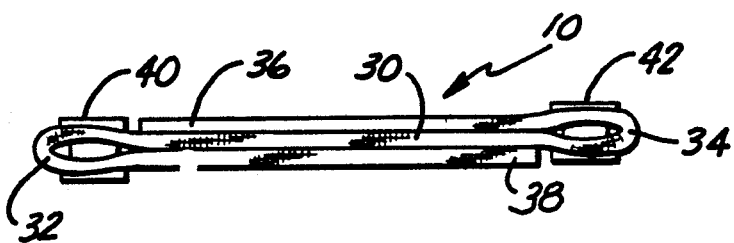
FIG. 4 is a side view of the prosthetic ligament of FIG. 2.
Figure 5:
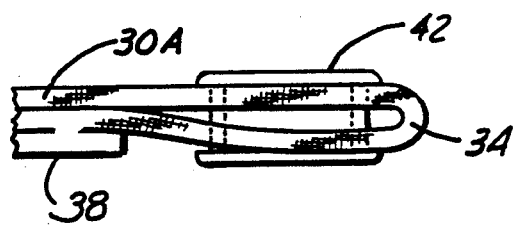
FIG. 5 is a detail view showing one end of the prosthetic ligament of FIG. 2.

Sacrificial layers 38 and 40 are fastened to load-bearing strap-like element 30 by any suitable mechanical, chemical or thermal means, such as sewing, glueing, or the like. As illustrated in FIGS. 2 and 3, a preferred method of bonding or connecting together layers 30, 36 and 38 is by sewing. This sewing can be done manually, or with machine. Sewing threads of any material meeting biocompatibility criteria can be used. In the case of sewing manually, a single thread is passed through the multiple layers 36, 30, and 38 in such a way as to bond or connect together all three layers. In the case of machine sewing, a needle thread and a separate bobbin thread are used to form a lock stitch which bonds or connects the layers together. Many different stitch patterns can be used to bond the layers. FIGS. 2 and 3 illustrate a preferred stitch pattern involving three parallel stitch lines 54, 56, and 58 along the length of device 10. Stitch lines 54, 56 and 58 are spaced equally across the width of device 10. Various sewing machines can be used for creating this pattern such as, for example, the Mitsubishi Industrial Sewing Machine Model PLK-1210.

Protective sacrificial areas 36 and 38 protect load-bearing layer 30 against abrasion. Areas 36 and 38 can themselves be further protected at key abrasion points by a further layer of woven fabric, non-woven fabric or film material, or by the addition (for example, by soaking) of an abrasion resistant material into layers 36 and 38.

Eyelets 40 and 42 are preferably inserted into loops 32 and 34 by starting a small opening in load-bearing strap-like element 30 and inserting the eyelet 40, 42 through the layers by compacting filaments about the eyelet 40, 42. Eyelets 40 and 42 may be formed of any suitable biocompatible material, and are preferably the same material as that used to form strap-like element 30. Eyelets 40 and 42 are shaped to receive and hold bone screws 46 and 48. If suturing or stapling is used, for fixation of the ends of device 10 rather than bone screws, eyelets 40 and 42 are not needed. Instead, the staples or sutures are passed through loops 32 and 34 at the opposite ends of device 10.

Figure 6A:
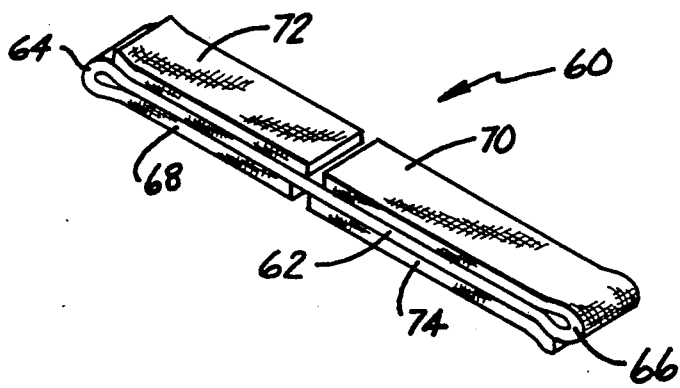
FIGS. 6A and 6B are perspective and side elevational views, respectively, of a second embodiment of the prosthetic ligament of the present invention.
Figure 6B:
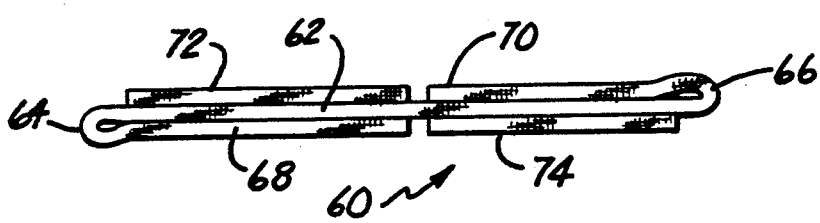

FIGS. 6A and 6B illustrate prosthetic device 60, which is a second embodiment of the present invention. In this embodiment, a single layer of strap-like material is folded over at each end to form load-bearing strap-like element 62, end loops 64 and 66, and loop tails 68 and 70. Abrasion resistant sacrificial layers 72 and 74 are bonded or connected to strap-like element 62 to perform sacrificial abrasion and protection of the load-bearing characteristics of strap-like element 62. By forming sacrificial layers 72 and 74 separate from the strap-like material which forms load-bearing element 62, end loops 64 and 66, and tails 68 and 70, it is possible to obtain superior abrasion resistant characteristics which may otherwise be attainable only by sacrificing other desired qualities of load-bearing element 62. In the embodiment shown in FIG. 7, bone screw receiving eyelets (similar to eyelets 40 and 42 of FIGS. 2-5) are not shown. Device 60 can be attached at its opposite ends by sutures or surgical staples. Alternatively, eyelets similar to eyelets 40 and 42 of FIGS. 2-5 can be provided in device 60.

Figure 7A:
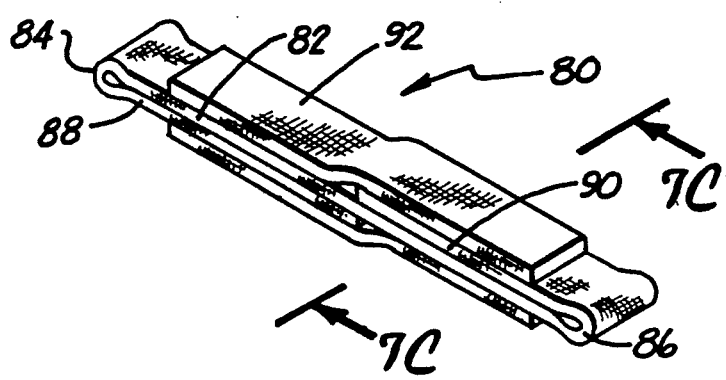

FIGS. 7A-7C show prosthetic device 80, which is a third embodiment of the present invention. In this embodiment, a continuous strap-like material is folded over to form load-bearing strap-like element 82, end loops 84 and 86, and tails 88 and 90. Covering (and bonded to) substantially the entire length of device 80 (except for end loops 84 and 86) is protective sacrificial sheath 92, which is in a C-shaped configuration to cover the top, the bottom, and one side of the strap-like material. Once again, because loops 84 and 86 are the portions of device 80 which are connected to the patient's body, load-bearing element 82 provides the load-bearing capabilities for device 80, while protective sheath 92 acts as a sacrificial abrasion layer for protecting load-bearing element 82 from abrasion due to contact with the patient's bones. Because it is not required to exhibit load-bearing characteristics, sheath 92 is preferably of a different material from the strap-like material forming load-bearing element 82 in order to maximize the abrasion resistant characteristics of device 80.

FIGS. 8A-8C show prosthetic device 100, which is still another embodiment of the present invention. In this embodiment, a continuous strap-like material is folded to produce a load-bearing strap-like element 102, end loops 104 and 106, and tails 108 and 110. Protective sleeve 112 extends around the strap-like material so that only end loops 104 and 106 extend out opposite ends of sleeve 112. The device is bonded together so that sleeve 112 is attached to the strap-like material forming strap-like element 102 and tails 108 and 110.

FIG. 9 illustrates prosthetic device 120, which is formed by a strap-like material doubled over to form upper and lower load-bearing layers 122 and 124 and end loop 126. Eyelet 128 extends through layers 122 and 124 at the end near loop 126. Sacrificial protective layer 130 is attached to the surface of load-bearing layer 124 from about the mid-point of device 120 to near the end containing eyelet 128. Device 120, as shown in FIG. 9, is useful where attachment is to be made at one end with a bone screw, and by sutures or surgical staples at an opposite end. Device 120 is also intended for those applications where an abrasion site will occur on only one side of the device. In other words, the particular application for device 120 will be typically different from the use of device 10 shown in FIG. 1 (where there are abrasion sites at different locations and on opposite sides of device 10).

The following examples are provided to illustrate the present invention. They are intended to be illustrative, and are not intended to limit the invention to any particular embodiment.

EXAMPLE 1

An abrasion resistant ligament generally of the type shown in FIGS. 2-5 was made as a flat braid constructed from bundles of polypropylene filaments. The filaments were formed by die extrusion of a polypropylene resin into a bundle of 180 filaments approximately 35 microns in diameter. The filament bundle had a tenacity of greater than 7.5 grams per denier.

The flat braid was then fabricated in an 8 mm width containing 13 bundles of filaments. The braid thickness was approximately 1.5 mm.

The prosthetic device was constructed, in accordance with FIGS. 2-5, by folding the braid into three layers and sewing the layers together using polypropylene thread. At the end of the sewing area, the braid was cut and heat sealed to prevent unraveling. Using this procedure, end loops 32 and 34 were formed, one at each end of the device as shown in FIGS. 2-5. In this particular example, eyelets 40 and 42, shown in FIGS. 1-5 were not provided.

The strength of the device was determined to be about 3300N using the loop ends for tensile loading.

EXAMPLE 2

Using the procedure of Example 1, a prosthetic device similar to device 10 of FIGS. 2-5 (including eyelets 40 and 42) was fabricated. Eyelets 40 and 42 were inserted through both layers in each loop section 32 and 34, respectively. The eyelets 40 and 42 were machined from a block of polypropylene into a shape that conformed with the head of a bone screw to be used for fixation. Placing the eyelets 40 and 42 through loops 32 and 34 at the ends of device 10 provided a high strength anchor for attachment to bone.

The strength of the device was determined to be 1800N using the eyelets for tensile loading. An additional device was prepared in the same manner and subjected to four million cycles of dynamic tensile loading and bending. The device exhibited no loss of strength, even though some abrasion was evident on protective layers 36 and 38.

EXAMPLE 3

Using the procedure of Example 2, a stronger device was prepared using a bulkier polypropylene braid that contained 26 bundles of the same filaments (rather than 13 bundles as used in examples 1 and 2). The strength of the device was determined to be 4500N using tee eyelets for tensile loading. This strength was sufficient to cause failure of the bone screws which were used for fixation before the device itself failed.

EXAMPLE 4

Using the procedure of Example 1, an abrasion resistant device was made. The device was then covered with an additional protective layer in the form of a tubular braid of polypropylene surrounding the device and sewn to the device as illustrated in FIGS. 8A-8C. The sewing was done with a sewing machine. The resulting structure was that of prosthetic device 100 illustrated in FIGS. 8A-8C.

EXAMPLE 5

Using a narrow fabric web of woven nylon, a device was made in a form similar to device 10 of FIG. 2, except the eyelets 40 and 42 were not provided in the loop ends. Nylon thread was used to sew the layers together. The sewing on each side extended only from the looped end to the center of the device. This simulates a complete loss of the sacrificial protective layer. The stength of the device was determined to be 1200N, using the loops for tensile loading. This experiment demonstrated that the strength of the prosthetic device is in the strap-like element, and that the sacrificial layers do not significantly contribute to the strength of the device.

EXAMPLE 6

Using the polypropylene braid for Example 1, an abrasion resistant device similar to that shown in FIGS. 6A and 6B was formed. Protective layers 72 and 74 were made of a woven narrow fabric nylon web.

EXAMPLE 7

A device made following the procedure of example 2 was used as a prosthetic replacement of the anterior cruciate ligament in a goat. Standard surgical practices were used in this replacement. The animal was allowed to recover and was maintained for two weeks, during which time the device functioned satisfactorily as a ligament replacement. In other words, it restored normal joint stability and range of joint motion. After two weeks, the animal was sacrificed, and the device was removed for evaluation. Gross examination of the knee showed the device to be well tolerated by the tissues. The device showed very slight wear of the protective sacrificial layer in the area of contact with the tibia, and was otherwise unaffected by the two week implantation.

CONCLUSION

The prosthetic device of the present invention offers significant advantages over prior art ligament and tendon prostheses. First, the device is protected from strength loss due to abrasion until a significant amount of material has been lost due to abrasion. Second, the device provides distinct areas for sacrificial abrasion. In the case of a prosthetic ligament for replacement of the anterior cruciate ligament, two distinct areas for sacrificial abrasion located on opposite sides of the device accomodate the two areas where abrasion against bone will occur. Third, the present invention also accomodates the use of high strength eyelets, which facilitate fixation of the prosthetic ligament to bone during surgery.

Although the present invention has been described with reference to preferred embodiments, workers skilled in the art will recognize that changes may be made in form and detail without departing from the spirit and scope of the invention.

What is claimed is:

1. A prosthetic device comprising:
   a flexible, load-bearing strap-like element of a stable biocompatible material, the strap-like element including a main load-bearing layer with first and second surface and first and second ends for attachment to a patient; and
   a first abrasion-resistant sacrificial layer attached to the first surface of the main load-bearing layer at a first position where abrasion between the prosthetic device and a bone of the patient occurs, the first sacrificial layer being capable of substantial sacrificial abrasion which does not substantially alter load-bearing capabilities of the strap-like element.

2. The prosthetic device of claim 1 wherein the strap-like element is transversely folded over at its first end to form the main load-bearing layer, a first loop and a first loop tail adjacent the first loop, the first loop tail being attached to the main load-bearing layer.

3. The prosthetic device of claim 2 wherein the strap-like element is transversely folded over at its second end to form a second loop and a second loop tail adjacent the second loop, the second loop tail being attached to the main load-bearing layer.

4. The prosthetic device of claim 3 wherein the first loop tail is attached to the first surface of the main load-bearing layer and the second loop tail is attached to the second surface of the main load-bearing layer.

5. The prosthetic device of claim 4 wherein the first sacrificial layer is integral with and extends beyond the first loop tail toward the second loop to cover a portion of the first surface of the main load-bearing layer.

6. The prosthetic device of claim 4 and further comprising:
   a second abrasion-resistant sacrificial layer attached to the second surface of the main load-bearing layer.

7. The prosthetic device of claim 6 wherein the second sacrificial layer is integral with and extends beyond the second loop tail toward the first loop to cover a portion of the second surface of the main load-bearing layer.

8. The prosthetic device of claim 7 wherein the first and second sacrificial layers and the first and second loop tails are attached to the main load-bearing layer by stitching.

9. The prosthetic device of claim 7 wherein the main load-bearing layer, the first and second loops, the first and second loop tails, and the first and second sacrificial layers are formed by a continuous length of biocompatible material.

10. The prosthetic device of claim 9 and further comprising:
    a first eyelet fixation device extending through two layers of material forming the first loop; and
    a second eyelet fixation device extending through two layers of material forming the second loop.

11. The prosthetic device of claim 9 wherein the biocompatible material is a braided material.

12. The prosthetic device of claim 11 wherein the braided material is constructed from a synthetic polymeric material.

13. The prosthetic device of claim 12 wherein the synthetic polymeric material is polypropylene.

14. The prosthetic device of claim 4 and further comprising:
    a first eyelet fixation device extending through two layers of material forming the first loop; and
    a second eyelet fixation device extending through two layers of material forming the second loop.

15. The prosthetic device of claim 4 wherein the first sacrificial layer is a part of a protective sacrificial sheath which covers and is attached to the first surface of the main load-bearing layer and the first loop tail, and which covers and is attached to the second surface of the main load-bearing layer and the second loop tail.

16. The prosthetic device of claim 15 wherein the protective sacrificial sheath is a sleeve positioned over the strap-like element so that the first loop extends out a first end of the sleeve and the second loop extends out the second end of the sleeve.

17. The prosthetic device of claim 2 and further comprising:
    a first eyelet fixation device extending through two layers of material forming the first loop.

18. The prosthetic device of claim 1 and further comprising:

a second abrasion-resistant sacrificial layer attached to the second surface of the main load-bearing layer at a second position where abrasion between the prosthetic device and a bone of the patient occurs, the second sacrificial layer being capable of substantial sacrificial abrasion which does not substantially alter the load-bearing capability of the strap-like element.

19. The prosthetic device of claim 1 wherein the strap-like element is formed by a biocompatible synthetic polymeric material.

20. A prosthetic device comprising:
a multilayer, flexible, load-bearing, strap-like element having a first main load-bearing layer extending between first and second ends, the strap-like element being folded over at the first end to form a first loop and a second layer which overlies and is attached to a first surface of the first layer wherein the second layer includes an abrasion-resistant sacrificial abrasion portion which protects the first surface of the first layer from abrasive contact with portions of a patient's skeletal/muscular system; and
means for attaching the first and second ends of strap-like element to spaced apart locations of the patient's skeletal/muscular system.

21. The prosthetic device of claim 20 wherein the strap-like element is folded over at the second end to form a second loop and a third layer which overlies and is attached to a second surface of the first layer.

22. The prosthetic device of claim 21 wherein the third layer includes a sacrificial abrasion portion which protects the second surface of the first layer from abrasive contact with portions of the patient's skeletal/muscular system.

23. The prosthetic device of claim 20 and further comprising:
a first eyelet fixation device extending through the first loop; and
wherein the means for attaching includes a bone screw for extending through the first eyelet fixation device to mount the first end of the strap-like element to a bone of the patient.

* * * * *